(12) United States Patent
Carver

(10) Patent No.: US 7,251,028 B2
(45) Date of Patent: Jul. 31, 2007

(54) SCANNING SPECTRUM ANALYZER

(75) Inventor: Gary Ernest Carver, Flemington, NJ (US)

(73) Assignee: Princeton Lightwave, Inc, Cranbury, NJ (US)

( * ) Notice: Subject to any disclaimer, the term of this patent is extended or adjusted under 35 U.S.C. 154(b) by 162 days.

(21) Appl. No.: 11/068,295

(22) Filed: Feb. 28, 2005

(65) Prior Publication Data

US 2006/0192971 A1 Aug. 31, 2006

(51) Int. Cl.
*G01J 3/06* (2006.01)
*G01J 3/28* (2006.01)
*G01J 3/18* (2006.01)

(52) U.S. Cl. .................. 356/328; 356/308; 356/334

(58) Field of Classification Search .......... 356/33, 356/32, 300, 302, 303, 305, 326, 328, 330, 356/334, 308; 359/744, 399, 362, 52; 250/353, 250/341.1
See application file for complete search history.

(56) References Cited

U.S. PATENT DOCUMENTS

| | | | |
|---|---|---|---|
| 4,815,849 A * | 3/1989 | Sullivan ................ | 356/328 |
| 5,305,083 A * | 4/1994 | Marianik et al. ........ | 356/332 |
| 5,889,588 A | 3/1999 | Santman et al. | |
| 6,002,822 A | 12/1999 | Strasser et al. | |
| 6,263,123 B1 | 7/2001 | Bishop et al. | |
| 6,337,737 B1 * | 1/2002 | Chang et al. .......... | 356/32 |
| 6,429,968 B1 * | 8/2002 | Carver ................ | 359/385 |
| 6,452,681 B1 * | 9/2002 | Carver et al. .......... | 356/450 |
| 7,035,505 B2 * | 4/2006 | Shen et al. ............ | 385/24 |
| 2003/0128359 A1 * | 7/2003 | Sanpei et al. .......... | 356/326 |
| 2005/0035295 A1 * | 2/2005 | Bouma et al. .......... | 250/341.1 |
| 2005/0105902 A1 * | 5/2005 | Alavie et al. .......... | 398/34 |

OTHER PUBLICATIONS

Yun, S.H. et al.—"High-speed wavelength-swept semiconductor laser with a polygon-scanner-based wavelength filter" -Optics Letters vol. 28 No. 20☐☐.*
Othonos, Andreas—"Fiber Bragg Gratings"—Rev. Sci. Instrum. 68(12), Dec. 1997. pp. 4322-4327.*
Simpson, Alexander G. et al.—"Optical sensor interrogation with a blazed fiber Bragg grating"—Applied Optics vol. 43, No. 1.*
R. Leitgeb et al., Performance of fourier domain vs. time domain optical coherence tomography, Apr. 21, 2003, vol. 11 No. 8, Optics Express, Vienna, Austria.
Kenichi Nakamura et al., High-Speed Optical Performance Monitor for WDM Network using MEMS Scanning Mirror, ANRITSU Corp., Japan.
Jill D. Berger et al., Widely tunable, narrow optical bandpass Gaussian filter using a silicon microactuator, Iolon Inc., San Jose, California.

(Continued)

*Primary Examiner*—Tarifur Chowdhury
*Assistant Examiner*—Daniel Cartoon
(74) *Attorney, Agent, or Firm*—DeMont & Breyer, LLC

(57) ABSTRACT

A system for spectral analysis of a multi-wavelength signal is disclosed. The illustrative embodiment of the present invention, like the prior art, uses a grating or prism to disperse the spectral components of a multi-wavelength signal, and then uses a reciprocating or rotating mirror to direct the spectral components, one at a time, into a photodetector. The illustrative embodiment uses a telescope between the grating and the mirror to improve the spectral resolution of the system.

22 Claims, 12 Drawing Sheets

OTHER PUBLICATIONS

Gordon Wilson et al., Spectral Filter with Independently Variable Center Wavelength and Bandwidth, European Conference on Optical Communications, Sep. 9, 2004, Sweden.

D.M. Maron et al., Wavelength-selective 1x2 switch utilizing a planar lightwave circuit stack and a MEMS micromirror array, Bell Lavoratories, Lucent Technologies, New Jersey.

* cited by examiner

SCANNING SPECTRUM ANALYZER

FIELD OF THE INVENTION

The present invention relates to optics in general, and, more particularly, to spectrum analyzers.

BACKGROUND OF THE INVENTION

The spectral analysis of multi-wavelength signals is vital in many fields. For example, in the field of telecommunications voice, data, and video signals are often transmitted on optical carriers of different wavelengths in optical fibers. In these systems, it is essential for the operators of an optical telecommunications system to be able to perform a high-resolution spectral analysis of its signals to ensure that they are within their intended operating parameters.

In the field of medicine, for example, optical coherence tomography (hereinafter "OCT") is a well known and widely-used technique for tissue sample analysis. One version of OCT, called Fourier-Domain Optical Coherence Tomography, involves the spectral analysis of the light scattered by a tissue sample. The widespread adoption of Fourier-Domain OCT has been limited, however, because the available systems are not capable of performing the spectral analysis at a level sufficient for many applications. Therefore, the need exists for a Fourier-Domain OCT system that has a higher spectral resolution than systems in the prior art.

SUMMARY OF THE INVENTION

The present invention enables the spectral analysis of a multi-wavelength signal without some of the costs and disadvantages for doing so in the prior art. For example, embodiments of the present invention are particularly well-suited for use in optical telecommunications systems and in Fourier-Domain Optical Coherence Tomography. Furthermore, it will be clear to those skilled in the art, after reading this disclosure, what the other applications are for embodiments of the present invention.

The illustrative embodiment of the present invention, like the prior art, uses a grating or prism to disperse the spectral components of a multi-wavelength signal, and then uses a reciprocating or rotating mirror to direct the spectral components, one at a time, into a photodetector. The photodetector is fast enough, in comparison to the movement of the mirror to enable many samples to be taken of the entire signal, which enables the intensity of the spectral components to be determined.

The incorporation of a telescope in the illustrative embodiment has several ramifications. First, the telescope relays the dispersive element onto the scanning mirror such that the mirror can sequentially direct each wavelength along the optical axis and into the center of the focusing lens. The fact that all wavelengths are on-axis and centered on the focusing lens enables the use of a focusing lens with a lower f/#, which causes the blur spot on the photodetector to be smaller than in the prior art. This improves the spectral resolution of the illustrative embodiment.

Second, the telescope magnifies the angular divergence of the beams that strike the mirror, which itself magnifies the spectral angular divergence of the light off of the mirror, which increases the effective spectral resolution of the illustrative embodiment.

Third, the telescope both (1) shrinks the width of the beams of light that strike the mirror, and (2) causes all of the beams of light to be coincident on the mirror, and both of these effects enable the embodiment to have a smaller mirror than in the prior art. The smaller mirror is advantageous because—all other things being equal—it can sweep the signal across the photodetector more quickly than a larger mirror and this enables the illustrative embodiment to have a greater temporal resolution than systems in the prior art.

The illustrative embodiment of the present invention comprises: a first device for radiating a first beam characterized by a first wavelength in a first direction and a second beam characterized by a second wavelength in a second direction, wherein the first wavelength is different than the second wavelength, and wherein the first direction is oblique to the second direction; and a second device for receiving the first beam and the second beam and for directing the first beam onto a locality from a third direction and the second beam onto the locality from a fourth direction, wherein the first beam arrives as collimated at the locality, wherein the second beam arrives as collimated at the locality, and wherein the third direction is oblique to the fourth direction.

DETAILED DESCRIPTION

Figure 1:
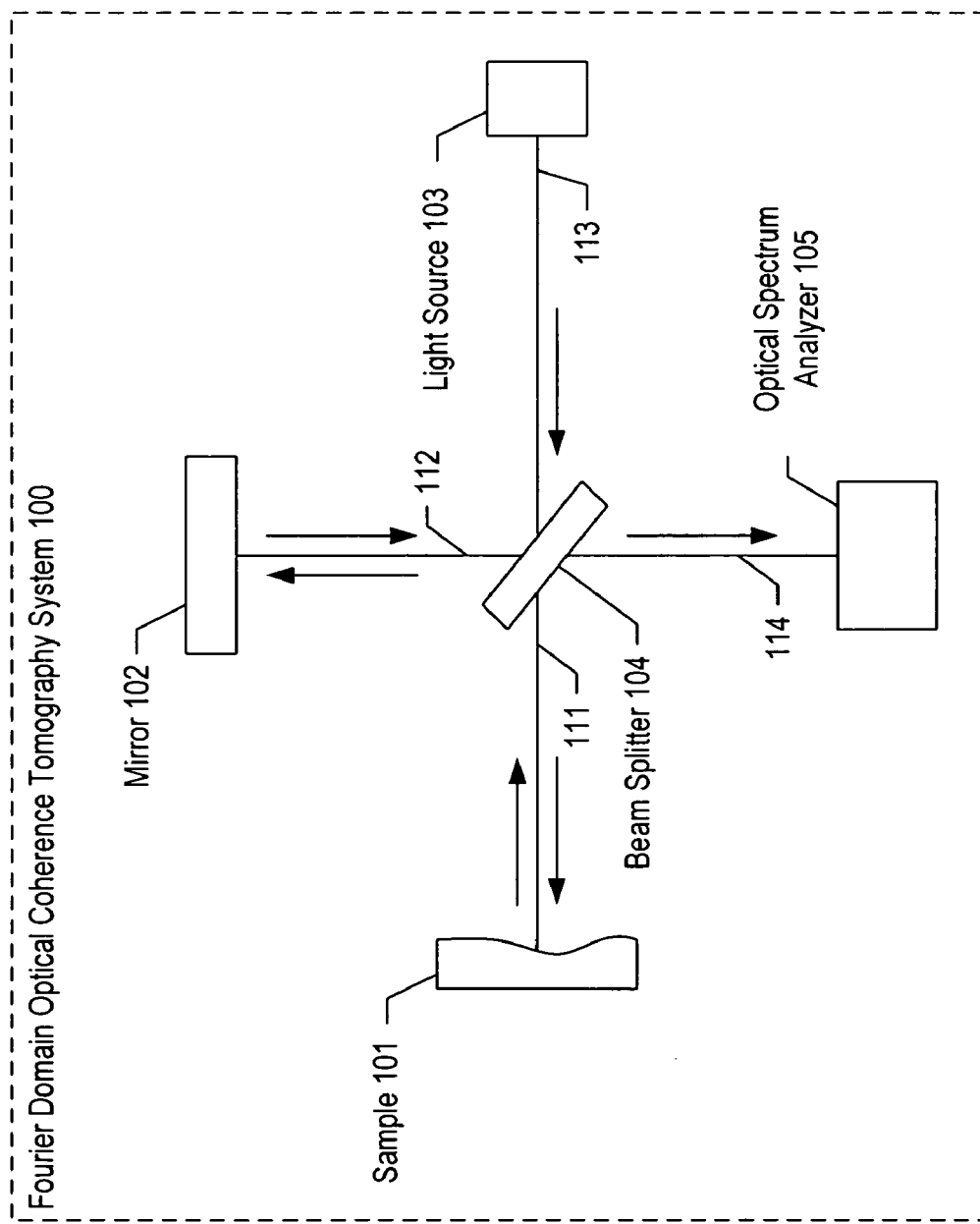
FIG. 1 depicts a schematic drawing of the salient aspects of a Fourier Domain Optical Coherence Tomography system in accordance with the illustrative embodiment of the present invention.

FIG. 1 depicts a schematic drawing of the salient aspects of a Fourier Domain Optical Coherence Tomography system in accordance with the illustrative embodiment of the present invention. Fourier Domain Optical Coherence Tomography system 100 comprises: sample 101, mirror 102, light source 103, beam splitter 104, and optical spectrum analyzer 105, interconnected as shown. The configuration is well known as a Michelson interferometer.

Sample 101 is a mass of biological tissue, which is to be analyzed in accordance with the illustrative embodiment of the present invention.

Mirror 102 is 1 cm by 1 cm and is reflective at 870 nm and is located at a fixed position as shown. It will be clear to those skilled in the art how to make and use mirror 102.

Light source 103 is a partially-coherent light source that emits a light beam characterized by a center wavelength of 870 nm and a spectral width of 40 nm. It will be clear to those skilled in the art how to make and use light source 103.

Beam splitter 104 is a 1 cm-wide by 1 cm-high by 0.5 cm-thick piece of glass which comprises surface coatings that are partially reflective for 870 nm-wavelength incident light. It will be clear to those skilled in the art how to make and use beam splitter 104.

Optical spectrum analyzer 104 is a system for separating and analyzing the spectral components contained in a multi-wavelength signal. Optical spectrum analyzer 104 is described in detail below and with respect to FIG. 2.

Light source 103 and beam splitter form source arm 113 of the Michelson interferometer. Beam splitter 104 and mirror 102 form reference arm 112 of the Michelson interferometer. Beam splitter 104 and sample 101 form sample arm 111 of the Michelson interferometer. Beam splitter 104 and optical spectrum analyzer 105 form detector arm 114 of the Michelson interferometer.

In operation, beam splitter 104 splits the light beam received from light source 103 into a reference and sample signal in reference arm 112 and sample arm 111, respectively. In reference arm 112, light is reflected back by mirror 102. In sample arm 111, light is reflected back by sample 101. Beam splitter 104 mixes the light from reference arm 112 and sample arm 111 and directs the combined light into detector arm 114 which conveys it to optical spectrum analyzer 105. Optical spectrum analyzer 105 discriminates and measures the intensities of the spectral components of the light in detector arm 114. The measurement of the intensities of the spectral components enables depth-localized measurement of sample 101, the measurement resolution of which is a function of the spectral resolution of optical spectrum analyzer 105.

Figure 2:
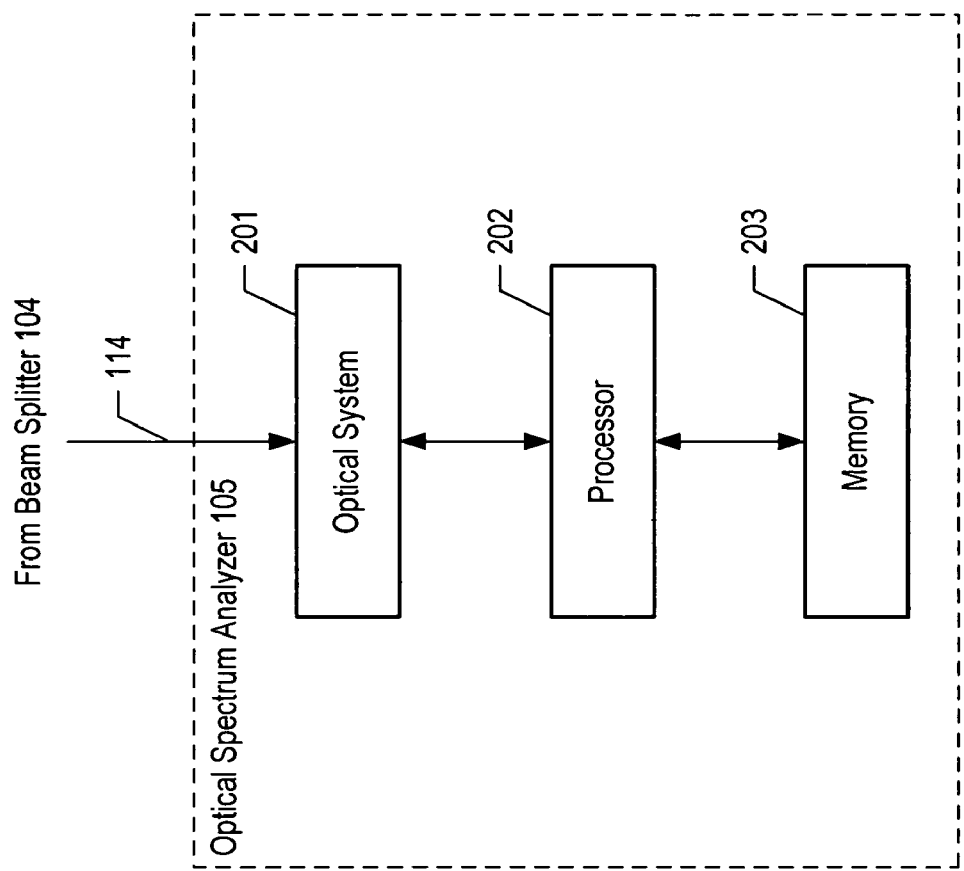
FIG. 2 depicts a block diagram of the salient components of optical spectrum analyzer 105 in accordance with the illustrative embodiment of the present invention.

FIG. 2 depicts a block diagram of the salient components of optical spectrum analyzer 105 in accordance with the illustrative embodiment of the present invention. Optical spectrum analyzer 105 comprises: optical system 201, processor 202, and memory 203, interconnected as shown.

Optical system 201 is a free-space optical system that is capable of resolving the spectral components of the light in detector arm 114 and reporting on the intensity of the components.

Processor 202 is a general-purpose processor that is capable of reading data and instructions from memory 203, of executing instructions, of writing data to memory 203, of receiving data from optical system 201, and of controlling optical system 201. It will be clear to those skilled in the art, after reading this specification, how to make and use processor 202.

Memory 203 is a non-volatile memory that is capable of storing data and instructions for processor 202 in well-known fashion.

Figure 3:
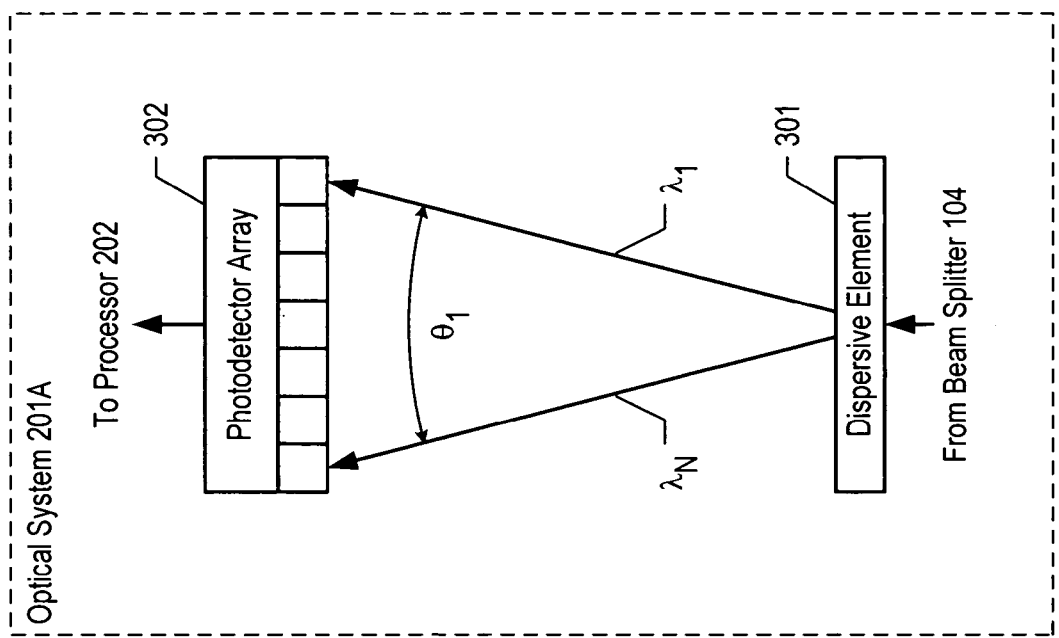
FIG. 3 depicts a schematic diagram of the salient components of optical system 201A in accordance with the prior art.

FIG. 3 depicts a schematic diagram of the salient components of optical system 201A in accordance with the prior art. Optical system 201A comprises dispersive element 301 and photodetector array 302, interrelated as shown.

Dispersive element 301 is a device that is capable of dispersing the spectral components of an optical signal so that each component emerges from dispersive element 301 at a different angle, depending on its wavelength, and collimated. To prevent FIG. 3 from being too cluttered, only those spectral components with the shortest and longest wavelengths (i.e., $\lambda_1$ and $\lambda_N$) are shown. As is well known in the prior art, dispersive element 301 is a free-space diffraction grating that receives a pre-collimated free-space optical signal.

Photodetector array 302 is a one-dimensional array of individual photodetectors, each of which is capable of generating an electrical signal based on the intensity of the light incident on that photodetector. Photodetector array 302 is positioned so that each spectral component emitted from dispersive element 301 is incident on and substantially fills a different photodetector. Each individual photodetector measures the intensity of the light that is incident on it and transmits a signal indicative of that intensity to processor 202.

An advantage of optical system 201A is that it is simple, inexpensive, and it can be made substantially immune to shock and vibration.

A disadvantage of optical system 201A is that the fixed spacing between the individual photodetectors prevents the full spectral content from being determined, which makes optical system 201A inappropriate for many applications. A further disadvantage is that photodetector arrays are expensive and the reliability of photodetector array 302 is lower than that of a single detector. A further disadvantage is that photodetector arrays are difficult to cool in order to reduce the thermal and shot noise that are inherent to photodetector.

Figure 4A:
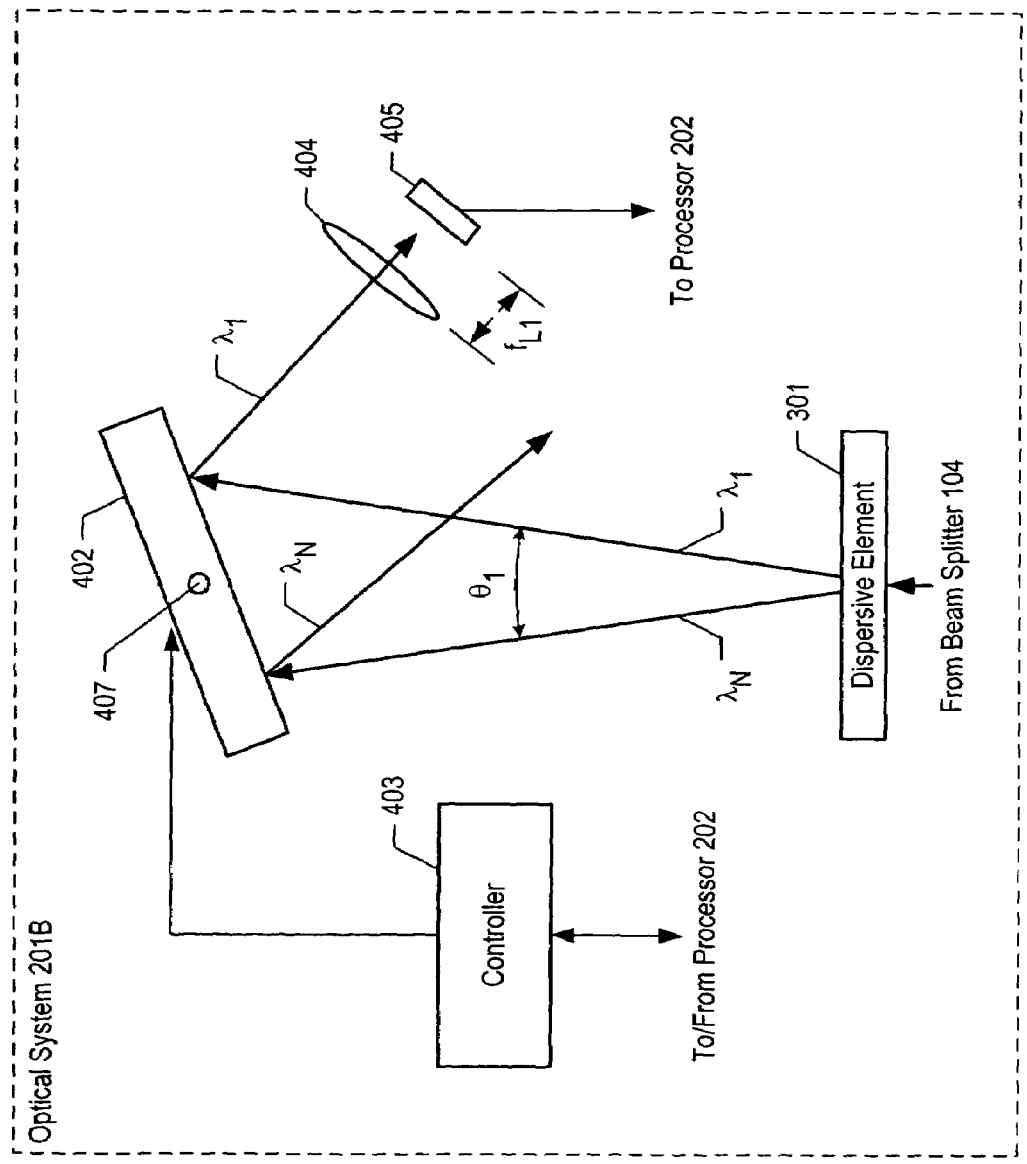
FIGS. 4A and 4B depict schematic diagrams of the salient components of optical system 201B in accordance with the prior art.
Figure 4B:
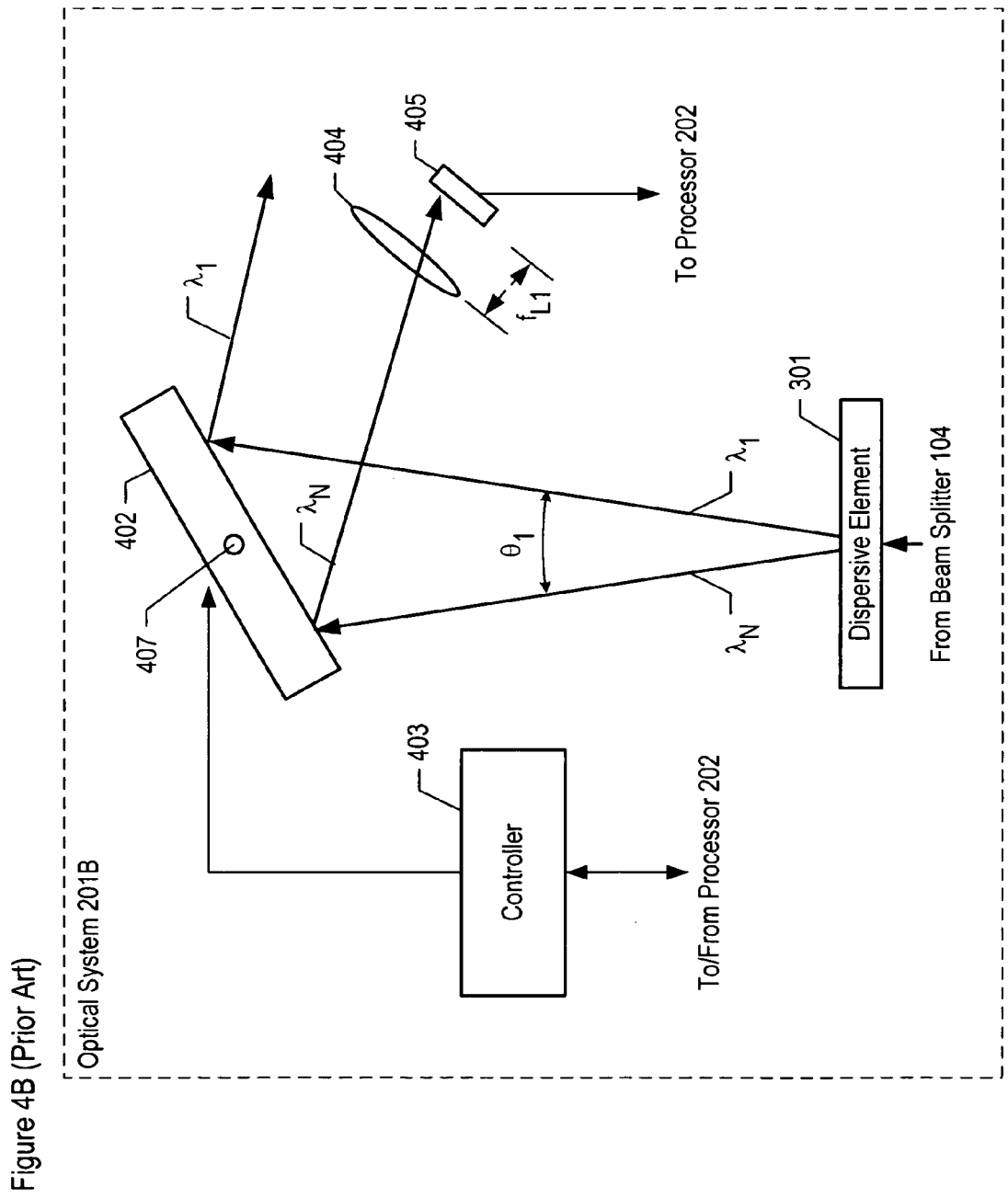

FIGS. 4A and 4B depict schematic diagrams of the salient components of optical system 201B in accordance with the prior art. Optical system 201B comprises: dispersive element 301, scanning mirror 402, controller 403, focusing lens 404, and photodetector 405, interrelated as shown.

Scanning mirror 402 is capable of rotation about rotation axis 407 and the face of scanning mirror 402 is 2 cm by 2 cm and reflective at 870 nm. Scanning mirror 402 receives beams $\lambda_1$ through $\lambda_N$ from dispersive element 301 and redirects them so that one of the N beams (e.g., $\lambda_1$ in FIG. 4) is directed toward lens 404 at any one time. The reflecting surface of scanning mirror 402 is sized so that all of the beams are reflected with minimal clipping. The angular position of scanning mirror 402 about rotation axis 407 determines which spectral component is received by lens 404. As shown in FIG. 4A, the angular position of scanning mirror 402 directs beam $\lambda_1$ into lens 404, and, as shown in FIG. 4B, the slightly rotated position of scanning mirror 402 directs beam $\lambda_N$ into lens 404. The rotation of scanning mirror 402 about rotation axis 407 is controlled via a control signal received from controller 403. It will be clear to those skilled in the art how to make and use scanning mirror 402.

Controller 403 is a general-purpose processor that receives a control signal from processor 202 and transmits a control signal to control the rotation of scanning mirror 402. The control signal from processor 202 instructs controller 403 to operate in either sweep mode or static mode. When controller 403 is in sweep mode, controller 403 instructs scanning mirror 402 to smoothly reciprocate around axis 407 so that all N beams are reflected and swept across focusing lens 404 during each half-cycle. When controller 403 is in static mode, controller instructs scanning mirror 402 to assume one angle and remain there, which reflects the desired beam into focusing lens 404. It will be clear to those skilled in the art how to make and use controller 403.

Focusing lens 404 is a thin convex lens with a clear aperture slightly larger than beam diameter $D_1$ (as described below and with respect to FIG. 5) and a focal length of $f_{L1}$.

The purpose of focusing lens 404 is to capture and focus the light reflected off of scanning mirror 402 into photodetector 405. Focusing lens 404 is positioned a distance of $f_{L1}$ from photodetector 405. Focusing lens 404 is positioned a sufficient distance from scanning mirror 402 so as to not impede the rotation of scanning mirror 402 and so that scanning mirror 402 is able to direct all of the spectral components through lens 404 and onto photodetector 405. The purpose of focusing lens 404 is to capture and focus the light reflected off of scanning mirror 402 into photodetector 405.

Photodetector 405 is a high-speed, low-noise, single-element photodetector that can be readily cooled to reduce thermal and shot noise. Photodetector 405 has a photodetection region which is slightly larger than the blur spot associated with the light received from lens 404. Photodetector 405 measures the intensity of the light that is incident on it and transmits a signal indicative of that intensity to processor 202.

An advantage of optical system 201B in comparison to optical system 201A is that the small size of photodetector 405 facilitates cooling to enable high-speed photodetection and low noise operation. In addition, acquisition of many data points from the single-element photodetector enables the measurement of more spectral components than can be measured using optical system 201A.

A disadvantage of optical system 201B is that scanning mirror 402 must be large in order to accommodate the spatially diverse spectral components that emanate from dispersive element 301 (as described below and with respect to FIG. 5). Large mirrors are unable to scan rapidly, which limits the temporal resolution of optical spectrum analyzer 201.

Figure 5:
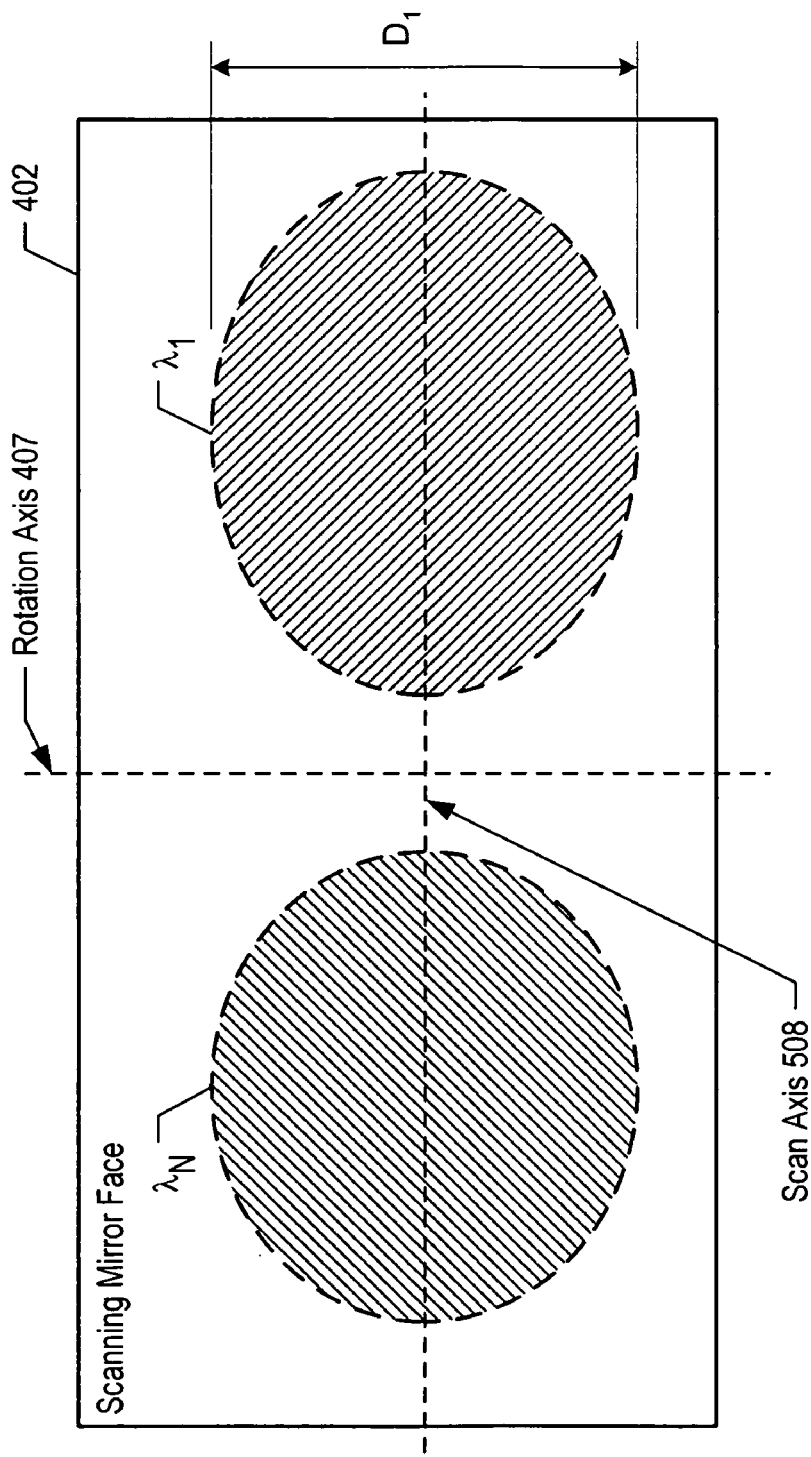
FIG. 5 depicts a drawing of the face of scanning mirror 402 and depicts the projection of the spectral components onto that face.

FIG. 5 depicts a drawing of the face of scanning mirror 402 and depicts the projection of the spectral components onto that face. To prevent FIG. 5 from being too cluttered, only those spectral components with the shorted and longest wavelengths (i.e., $\lambda_1$ and $\lambda_N$) are shown.

The separation of the projections of $\lambda_1$ and $\lambda_N$ on the face of scanning mirror 402 is a function of their angular divergence upon emission from dispersive element 301 and the distance that separates dispersive element 301 and scanning mirror 402. Additionally, in order to avoid clipping of the spectral components, the face must be larger in the direction of rotation axis 407 than the diameter $D_1$ of the collimated beams. For the purposes of this disclosure, the diameter of a beam is defined as the full width at half-maximum intensity. Further, in the direction of scan axis 508, the projection of each beam is enlarged due to the mirror angle. Therefore, the mirror face must be sufficiently large to avoid clipping in that direction as well.

Figure 6A:
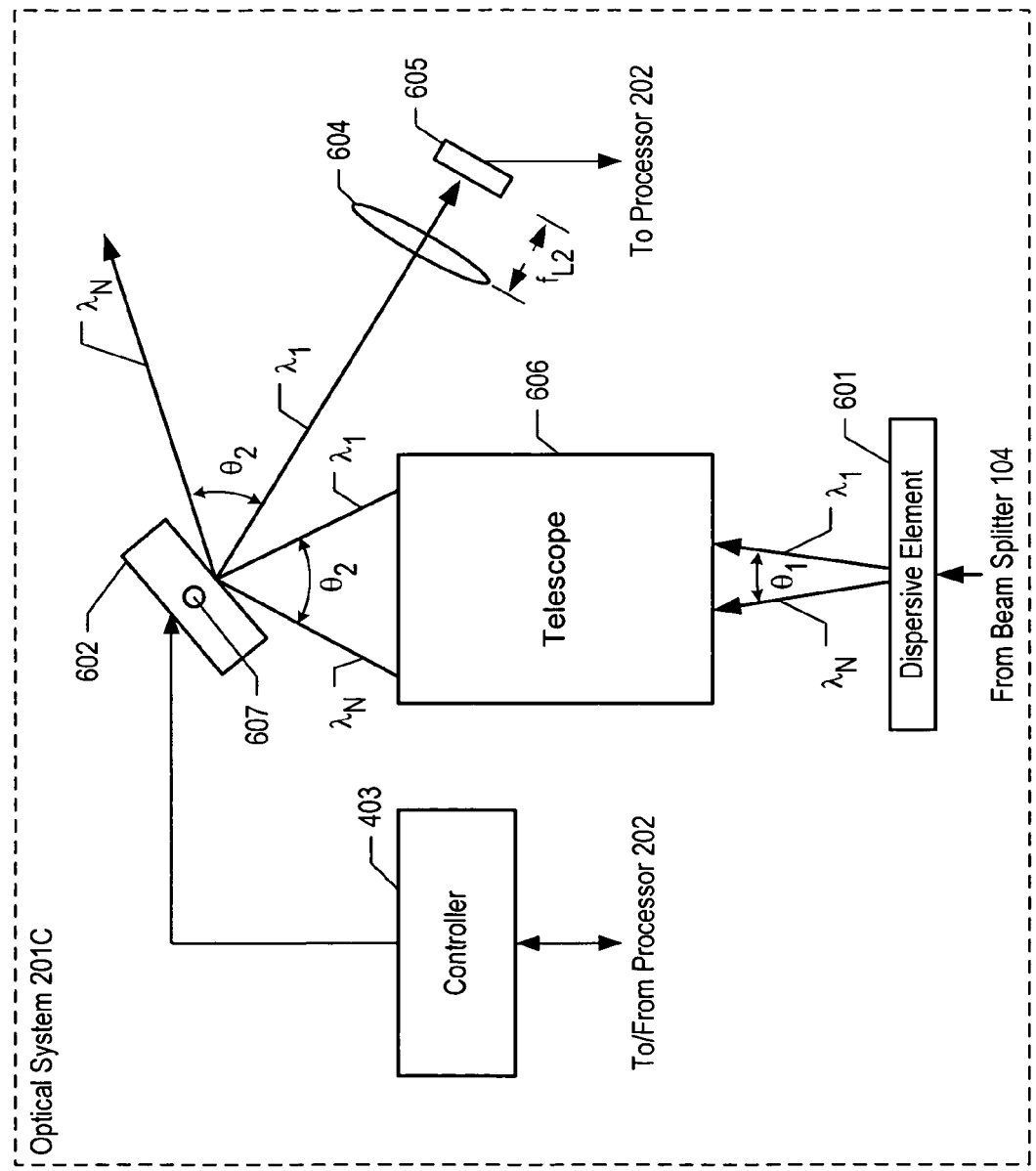
FIGS. 6A and 6B depict schematic diagrams of the salient components of optical system 201C in accordance with the illustrative embodiment of the present invention.
Figure 6B:
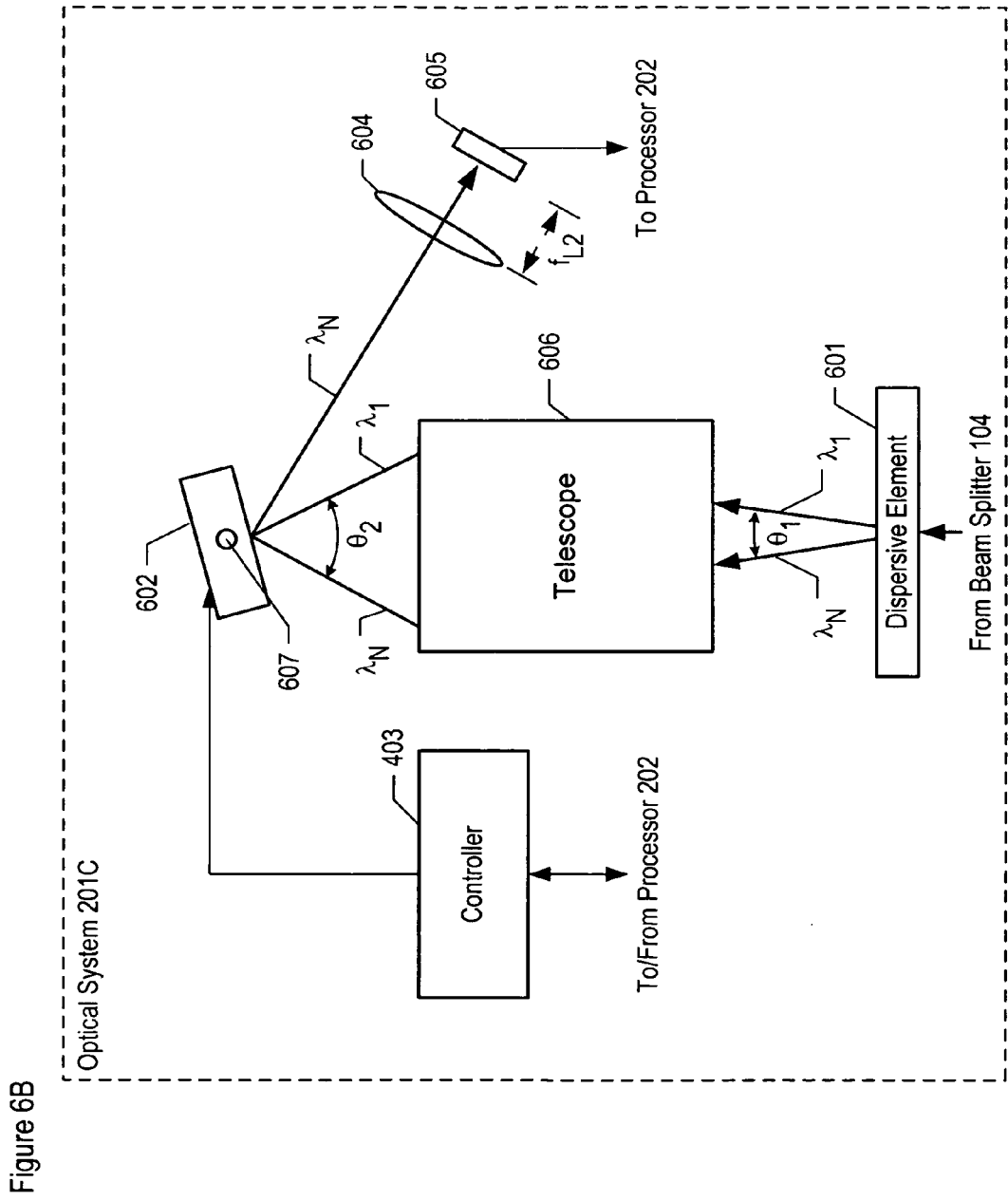

FIGS. 6A and 6B depict schematic diagrams of the salient components of optical system 201C in accordance with the illustrative embodiment of the present invention. Optical system 201C comprises: dispersive element 601, scanning mirror 602, controller 403, focusing lens 604, photodetector 605, and telescope 606, interrelated as shown.

Source 601 is a fiber Bragg grating, which launches the spectral components of an optical signal into free-space as collimated light. In some alternative embodiments, source 601 is a free-space diffraction grating which receives a pre-collimated free-space optical signal. In yet some other alternative embodiments, source 601 is a prism that receives a pre-collimated free-space optical signal. In yet some other alternative embodiments, source 601 is a holographic element that receives a free-space optical signal. In yet some other alternative embodiments, source 601 is a plurality of dispersive elements that includes:

i. prisms; or
ii. fiber Bragg gratings; or
iii. free-space diffraction gratings; or
iv. holographic elements; or
v. any combination of i, ii, iii, and iv.

It will be clear to those skilled in the art how to make and use source 601.

Scanning mirror 602 is an actuated mirror that is capable of turning about rotation axis 607 under the control of controller 403. The reflective face of scanning mirror 602 is 0.5 cm-high by 0.6 cm-wide and is reflective at 870 nm. The reflecting surface of scanning mirror 602 is sized so that all beams are reflected with minimal clipping. Although the illustrative embodiment comprises a scanning mirror to select which beam is directed into photodetector 605, it will be clear to those skilled in the art, after reading this specification, how to make and use alternative embodiments of the present invention in which a scanning prism or acousto-optic scanner is used instead of the scanning mirror.

Focusing lens 604 is a thin convex lens with a clear aperture slightly larger than beam diameter $D_2$ (as described below and with respect to FIG. 8) and a focal length of $f_{L2}$. Focusing lens 604 is positioned a distance of $f_{L2}$ from photodetector 605. Focusing lens 604 is positioned a sufficient distance from scanning mirror 602 so as to not impede the rotation of scanning mirror 602 and scanning mirror 602 is able to direct all desired spectral components toward focusing lens 604. The purpose of focusing lens 604 is to capture and focus the light reflected off of scanning mirror 602 into photodetector 605.

Photodetector 605 is a small-area, high-speed, low-noise, single-element photodetector, which can be readily cooled to reduce thermal and shot noise. Photodetector 605 has a photodetection region which is slightly larger than the blur spot associated with the light received from lens 604. Photodetector 605 measures the intensity of the light that is incident on it and transmits a signal indicative of that intensity to processor 202. Because beam diameter $D_2$ is smaller than beam diameter $D_1$, lens 604 and photodetector 605 can be smaller than lens 404 and photodetector 405.

Telescope 606 is an afocal optical element whose axis is orthogonal to the rotational axis of scanning mirror 602. The function of telescope 606 is three-fold. First, telescope 606 shrinks the width of the beams of light that strike the mirror, which enables the illustrative embodiment to have a smaller mirror than in the prior art. Second, telescope 606 causes all of the beams of light to be coincident on the mirror, which also enables the illustrative embodiment to have a smaller mirror than in the prior art. And third, telescope 606 magnifies the angular divergence of the beams that strike the mirror, which itself magnifies the spectral angular divergence of the light off of the mirror, which increases the spectral resolution of the illustrative embodiment. Telescope 606 is described below and with respect to FIGS. 7 and 8.

Dispersive element 601, telescope 606, scanning mirror 602, focusing lens 604, and photodetector 605 define an optical path, the axis of which includes crossing point 703. The distance of telescope 606 from dispersive element 601 on the optical path is such that telescope 606 captures all N beams emitted from dispersive element 601 without the occurrence of clipping. The distance of telescope 606 from scanning mirror 602 is such that crossing point 703 (as described below and with respect to FIG. 7) of telescope 606 is on the reflective surface of scanning mirror 602.

It will be clear to those skilled in the art, after reading this disclosure, how to make and use alternative embodiments of the present invention wherein crossing point 703 is not on the reflective surface of scanning mirror 602.

An advantage of optical system 201C in comparison to optical system 201A is that on-axis propagation of each wavelength into lens 604 allows for a smaller blur disk at photodetector 605. The smaller blur disk allows photodetector 605 to be small, facilitating its cooling and enabling high-speed photodetection with lower noise operation.

An advantage of optical system 201C in comparison to optical system 201B is that the beam diameters of the beams received by scanning mirror 602 are smaller than those received by scanning mirror 402 and all of the centers of beams $\lambda_1$ through $\lambda_N$ cross at crossing point 703, thus allowing the use of a smaller and faster scanning mirror which increases the temporal resolution of the system.

A further advantage of optical system 201C in comparison to optical system 201B is that telescope 606 magnifies the angular divergence of beams $\lambda_1$ through $\lambda_N$ as received by scanning mirror 602 (as described below and with respect to FIG. 7), which thereby improves the spectral resolution of optical spectrum analyzer 105.

A further advantage of optical system 201C in comparison to optical system 201B is that the small diameter of the beams received by focusing lens 604 enables the use of focusing lens 604 and photodetector 605 that are smaller-area than lens 404 and photodetector 405. Smaller components lead to lower cost, simpler packaging. In addition, its smaller size makes photodetector 602 easier to cool than photodetector 405 thereby improving its optical signal to noise ratio.

A further advantage of optical system 201C in comparison to optical systems 201A and 201B is that its ability to enable fast spectra generation and the use of a single-element photodetector enables the generation of a large number of data points per spectrum, which in turn enables deconvolution of the optical transfer function of optical system 201C from the output spectrum, which thereby results in a more accurate representation of the spectrum of the input signal.

A further advantage of optical system derives from the abundance of data points per spectrum. The angular dispersion of the output of any diffraction grating contains a sinusoidal dependency. The acceleration and deceleration of scanning mirror 602 during rocking motion naturally leads to a substantially sinusoidal variation in the number and distribution of the data points taken during each half-cycle of motion. The abundance of data points enables compensation for the sinusoidal variation of the output of fiber Bragg grating 601. In addition, the motion of scanning mirror 602 can be further controlled to improve compensation further.

Figure 7:
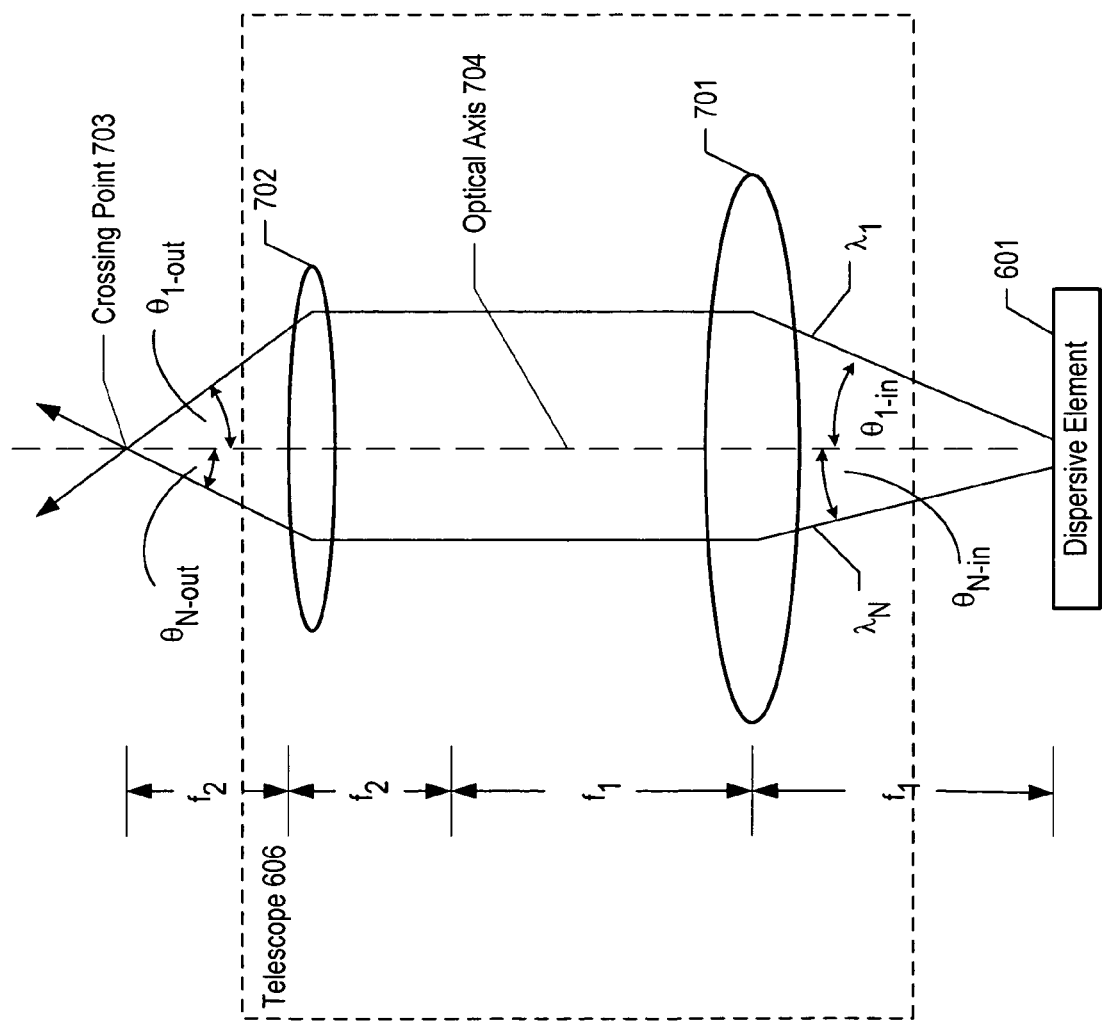
FIG. 7 depicts a schematic diagram of the salient components of telescope 606 and specifically depicts how telescope 606 manipulates the center rays of beams $\lambda_1$ and $\lambda_N$.

FIG. 7 depicts a schematic diagram of the salient components of telescope 606 and specifically depicts how telescope 606 manipulates the center rays of beams $\lambda_1$ and $\lambda_N$. To prevent FIG. 7 from being too cluttered, only those spectral components with the shorted and longest wavelengths (i.e., $\lambda_1$ and $\lambda_N$) are shown. Telescope 606 comprises lens 701 and lens 702, which are coaxial.

Lens 701 is a thin convex lens with a focal length equal to $f_1$, and lens 702 is a thin convex lens with a focal length equal to $f_2$. Lens 701 and lens 702 are coaxial with optical axis 704 and are held apart at a distance of $f_1+f_2$.

As FIG. 7 depicts, the center rays of beams $\lambda_1$ and $\lambda_N$ enter telescope 701 diverging at the angles of $\theta_{1\text{-}in}$ and $\theta_{N\text{-}in}$, respectively, with respect to optical axis 704, and emerge from telescope 701 converging at an angle of $\theta_{1\text{-}out}$ and $\theta_{N\text{-}out}$, respectively, wherein $\theta_{i\text{-}out} > \theta_{i\text{-}in}$, for i=1 through N. The ratio of $\theta_{i\text{-}out}$ to $\theta_{i\text{-}in}$ is a function of $f_1$ and $f_2$, and $\theta_{i\text{-}out}$ is equal to:

$$\theta_{i-out} = \tan^{-1}\left(\frac{f_1 \tan \theta_{i-in}}{f_2}\right) \qquad \text{(Eq. 1)}$$

and, therefore, $\theta_{i\text{-}out}/\theta_{i\text{-}in}$ is approximately equal to $f_1/f_2$, for small values of $\theta_{i\text{-}in}$ and $\theta_{i\text{-}out}$.

Figure 8:
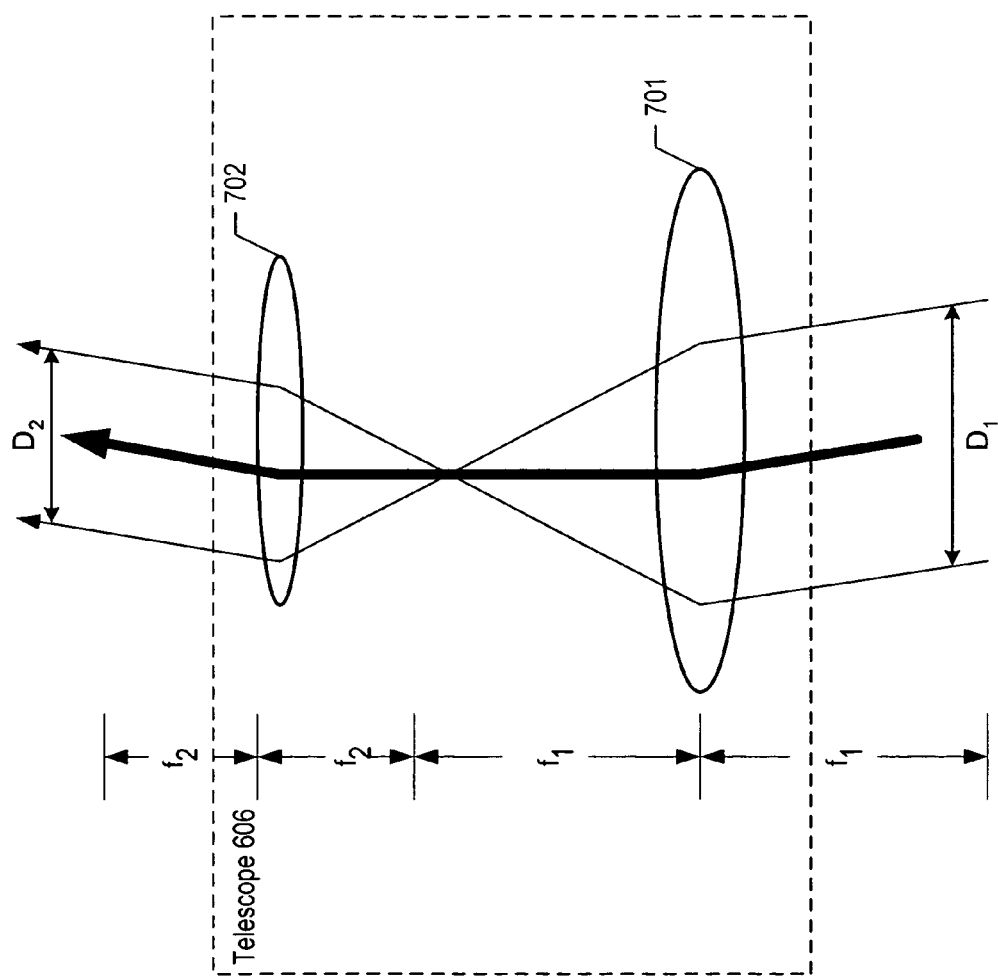
FIG. 8 depicts a schematic diagram of the salient components of telescope 606 and specifically depicts how telescope 606 manipulates beam $\lambda_N$.

FIG. 8 depicts a schematic diagram of the salient components of telescope 606 and specifically depicts how telescope 606 manipulates beam $\lambda_N$. To prevent FIG. 8 from being too cluttered, only the center and outer rays of beam $\lambda_N$ are shown.

As FIG. 8 depicts, beam $\lambda_N$ enters telescope 606 with a beam diameter of $D_1$ and emerges from telescope 606 with a beam diameter of $D_2$. The ratio of $D_2$ to $D_1$ is a function of $f_1$ and $f_2$, the focal lengths of lens 701 and lens 702 respectively, and $D_2$ is equal to:

$$D_2 = D_1\left(\frac{f_2}{f_1}\right) \qquad \text{(Eq. 2)}$$

Figure 9:
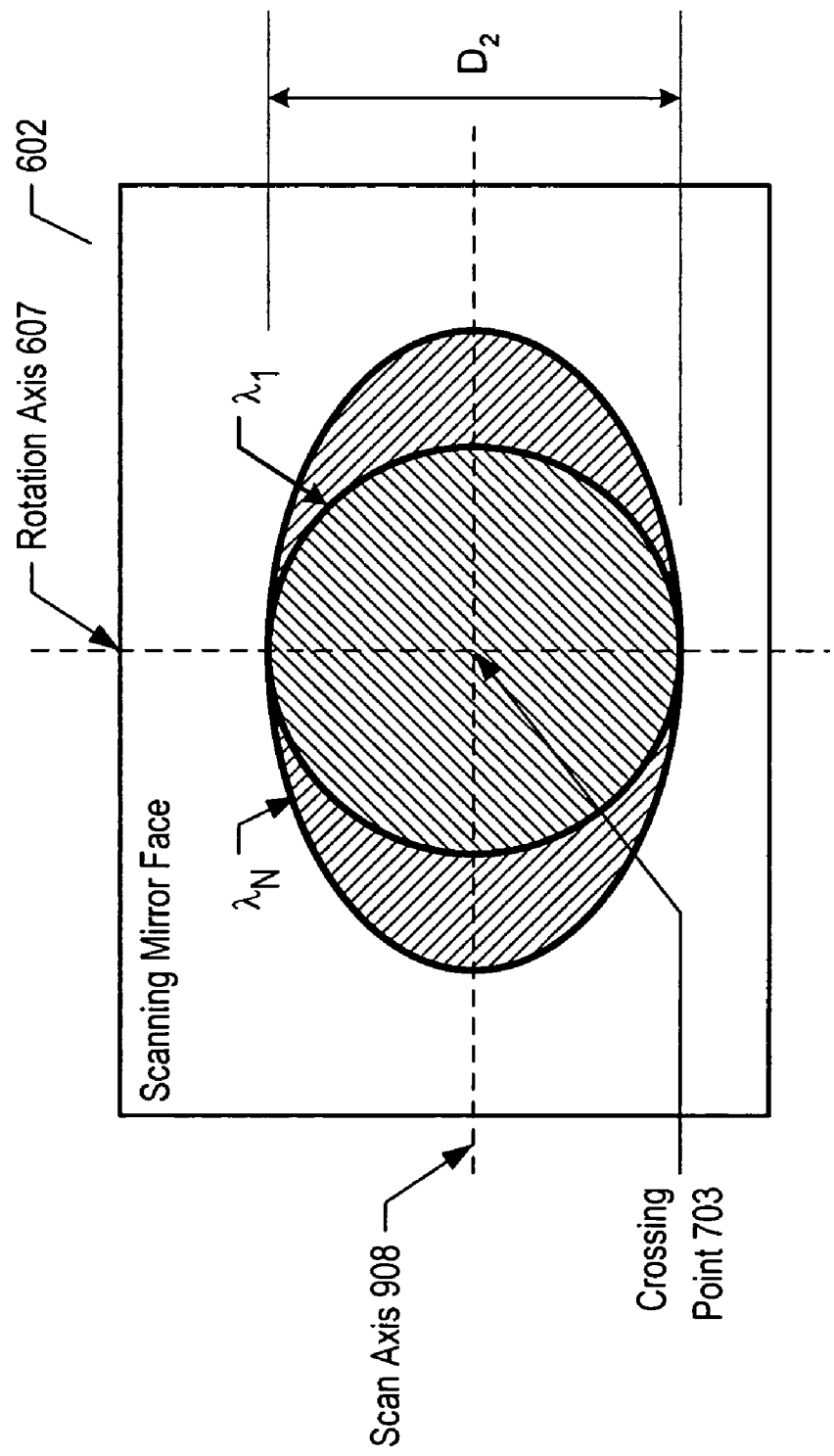
FIG. 9 depicts a drawing of the face of scanning mirror 602 and depicts the projection of the spectral components onto that face.

FIG. 9 depicts a drawing of the face of scanning mirror 602 and depicts the projection of the spectral components onto that face. To prevent FIG. 9 from being too cluttered, only those spectral components with the shortest and longest wavelengths (i.e., $\lambda_1$ and $\lambda_N$) are shown.

The center ray of the projections of $\lambda_1$ and $\lambda_N$ on the face of scanning mirror 602 are coincident with crossing point 703. Their width of their projection in the direction of rotation axis 607 is equal to beam diameter $D_2$. Their projection along scan axis 908 is elongated by the angle of the mirror with respect to their propagation direction. For example, the projection of beam $\lambda_N$ on the face is more elliptical than the projection of $\lambda_1$ since it hits the face at a larger angle. In order to avoid clipping of the spectral components, the face of scanning mirror 602 is made slightly larger in the direction of scan axis 908 than in the direction of rotation axis 607.

Figure 10:
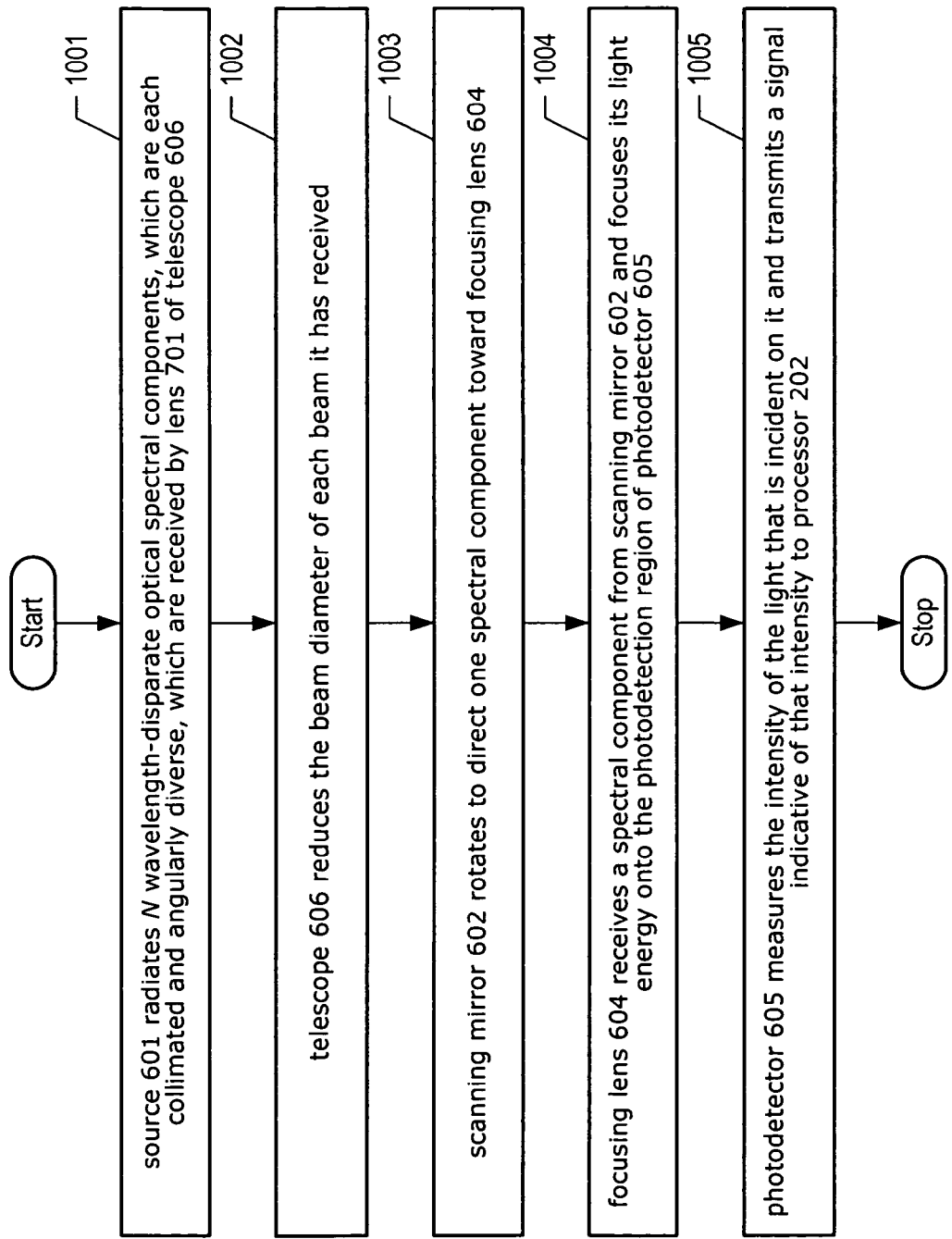
FIG. 10 depicts a flowchart of the salient processes performed by the illustrative embodiment of the present invention.

FIG. 10 depicts a flowchart of the salient processes performed by the illustrative embodiment of the present invention.

At task 1001, source 601 radiates N wavelength-disparate optical spectral components, which are each collimated and angularly diverse. The spectral components are received by lens 701 of telescope 606.

At task 1002, telescope 606 reduces the beam diameter of each beam it has received. When telescope receives a beam, it has a diameter of $D_1$, and when the beam emerges from telescope 606, it has a diameter of $D_2$, which is smaller than $D_1$, as described above and with respect to FIG. 8.

At task 1003, scanning mirror 602 rotates to direct one spectral component toward focusing lens 604.

At task 1004, focusing lens 604 receives a spectral component from scanning mirror 602 and focuses its light energy onto the photodetection region of photodetector 605.

At task 1005, photodetector 605 measures the intensity of the light that is incident on it and transmits a signal indicative of that intensity to processor 202.

It is to be understood that the above-described embodiments are merely illustrative of the present invention and that many variations of the above-described embodiments can be devised by those skilled in the art without departing from the scope of the invention. For example, in this Disclosure, numerous specific details are provided in order to provide a thorough description and understanding of the illustrative embodiments of the present invention. Those skilled in the art will recognize, however, that the invention can be practiced without one or more of those details, or with other methods, materials, components, etc.

Furthermore, in some instances, well-known structures, materials, or operations are not shown or described in detail to avoid obscuring aspects of the illustrative embodiments. It is understood that the various embodiments shown in the Figures are illustrative, and are not necessarily drawn to scale. Reference throughout the disclosure to "one embodiment" or "an embodiment" or "some embodiments" means that a particular feature, structure, material, or characteristic described in connection with the embodiment(s) is included in at least one embodiment of the present invention, but not necessarily all embodiments. Consequently, the appearances of the phrase "in one embodiment," "in an embodiment," or "in some embodiments" in various places throughout the Disclosure are not necessarily all referring to the same embodiment. Furthermore, the particular features, structures, materials, or characteristics can be combined in any suitable manner in one or more embodiments. It is therefore intended that such variations be included within the scope of the following claims and their equivalents.

What is claimed is:

1. An apparatus comprising:
    a first device for radiating a first beam characterized by a first wavelength in a first direction and a second beam characterized by a second wavelength in a second direction, wherein said first wavelength is different than said second wavelength, and wherein said first direction is oblique to said second direction;
    a second device for receiving said first beam and said second beam and for directing said first beam onto a locality from a third direction and said second beam onto said locality from a fourth direction, wherein said first beam arrives as collimated at said locality, wherein said second beam arrives as collimated at said locality, and wherein said third direction is oblique to said fourth direction; and
    a third device for receiving said first beam and said second beam at said locality, wherein said third device comprises a mirror having a rotation axis, and wherein said mirror is capable of axial motion about said rotation axis, and further wherein the reflecting face of said mirror and said rotation axis are substantially coplanar.

2. The apparatus of claim 1 wherein said first device comprises at least one prism.

3. The apparatus of claim 1 wherein said first device comprises at least one diffraction grating.

4. The apparatus of claim 1 wherein said first device comprises at least one fiber Bragg grating.

5. The apparatus of claim 1 wherein said first device comprises at least one holographic element.

6. The apparatus of claim 1 wherein said second device comprises an a focal telescope.

7. The apparatus of claim 1 further comprising:
    a fourth device for receiving one of said first beam and said second beam;
    wherein said third device directs said one of said first beam and said second beam toward said fourth device.

8. The apparatus of claim 7 wherein said fourth device comprises a photodetector.

9. The apparatus of claim 8 wherein said photodetector comprises one photodetection region.

10. The apparatus of claim 7 wherein said fourth device comprises an optical fiber.

11. The apparatus of of claim 1 further comprising a controller for controlling the angular position of said mirror about said rotation axis.

12. An apparatus comprising:
    a photodetector;
    an optical element for receiving a first beam from a first direction and a second beam from a second direction and for directing said first beam in a third direction and said second beam in a fourth direction, wherein said third direction and said fourth direction intersect at a crossing point, wherein said first beam and said second beam arrive as collimated at said crossing point; and
    a mirror for receiving said first beam and said second beam at said crossing point and directing one of said first beam and said second beam to said photodetector, wherein said mirror has a rotation axis, and wherein said mirror is capable of axial motion about said rotation axis, and further wherein the reflecting face of said mirror and said rotation axis are substantially coplanar.

13. The apparatus of claim 12 further comprising a fiber Bragg grating for radiating said first beam in said first direction and a second beam characterized by a second wavelength in said second direction, wherein said first beam is characterized by a first wavelength, and wherein said second beam is characterized by a second wavelength, and wherein said first wavelength is different than said second wavelength, and further wherein said first direction is oblique to said second direction.

14. The apparatus of claim 12 further comprising a controller for controlling the angular position of said mirror about said rotation axis.

15. The apparatus of claim 12:
    wherein said first beam is collimated and has a first diameter as received by said optical element;
    wherein said second beam is collimated and has a second diameter as received by said optical element;
    wherein said first beam arrives at said mirror with a third diameter;
    wherein said second beam arrives at said mirror with a fourth diameter;
    wherein said third diameter is narrower than said first diameter; and
    wherein said fourth diameter is narrower than said second diameter.

16. The apparatus of claim 12 wherein said optical element comprises an afocal telescope.

17. A method comprising:
    providing a mirror having a rotation axis, wherein said mirror is capable of axial motion about said rotation axis, and wherein the reflecting face of said mirror and said rotation axis are substantially coplanar;
    receiving a first beam at said mirror, wherein said first beam is received from an optical element along a first direction, and wherein said first beam is characterized by a first wavelength; and
    receiving a second beam at said mirror, wherein said second beam is received from said optical element along a second direction, and wherein said second beam is characterized by a second wavelength, and wherein said first direction is oblique to said second direction, and wherein said first beam and said second beam are substantially concentric at said mirror.

18. The method of claim 17 further comprising controlling the axial position of said mirror about said rotation axis to direct only one of said first beam and said second beam to a photodetector.

19. The method of claim 18 further comprising focusing said only one of said first beam and said second beam into said photodetector.

20. The method of claim 17 further comprising radiating said first beam and said second beam, wherein said first beam and said second beam are radiated by a wavelength dispersion element.

21. The method of claim 20 further comprising receiving said first beam and said second beam from said wavelength dispersion element at an optical element;

directing said first beam in said first direction; and directing said second beam in said second direction;

wherein said first beam is directed in said first direction and said second beam is directed in said second direction by said optical element.

22. The method of claim 17 further comprising oscillating the axial position of said mirror about said rotation axis to repeatedly and sequentially direct each of said first beam and said second beam to a photodetector.

* * * * *